US006479696B1

(12) United States Patent
Knebel et al.

(10) Patent No.: US 6,479,696 B1
(45) Date of Patent: Nov. 12, 2002

(54) METHOD FOR SYNTHESIS AND PROCESS INHIBITION OF ISOBORNYL (METH) ACRYLATE

(75) Inventors: Joachim Knebel, Alsbach-Haehnlein (DE); Doris Saal, Bensheim (DE)

(73) Assignee: Roehm GmbH & Co KG, Darmstadt (DE)

( * ) Notice: Subject to any disclaimer, the term of this patent is extended or adjusted under 35 U.S.C. 154(b) by 52 days.

(21) Appl. No.: 09/610,620

(22) Filed: Jul. 5, 2000

(30) Foreign Application Priority Data

Jul. 5, 1999 (DE) .......................... 199 30 721

(51) Int. Cl.$^7$ .......................... C07C 67/02; C07C 69/52
(52) U.S. Cl. ...................... 560/217; 560/220
(58) Field of Search ................. 560/217, 220

(56) References Cited

U.S. PATENT DOCUMENTS

| 2,129,694 A | * | 9/1938 | Izard et al. |
| 2,445,925 A | * | 7/1948 | Rebherg et al. |
| 2,458,888 A | * | 1/1949 | Rebherg et al. |
| 4,556,728 A | * | 12/1985 | Farrar et al. |
| 4,672,105 A | * | 6/1987 | Schlosser et al. |
| 4,745,213 A | * | 5/1988 | Schlosser et al. |
| 4,791,221 A | * | 12/1988 | Gabillet et al. |
| 4,916,255 A | * | 4/1990 | Kobayashi et al. ......... 560/217 |
| 4,983,761 A | * | 1/1991 | Breuer et al. |
| 5,072,027 A | * | 12/1991 | Kobayashi et al. |
| 5,362,904 A | * | 11/1994 | Kearns et al. |
| 5,399,744 A |   | 3/1995 | Pfirmann et al. |
| 6,008,404 A | * | 12/1999 | Miller et al. |

FOREIGN PATENT DOCUMENTS

EP          0 781 758 A       7/1997

OTHER PUBLICATIONS

Morrison, Robert T ; Boyd, Robert N, Organic Chemistry, fifth edition, Allyn and Bacon, Inc, Massachusetts, 1987.*
Aldrich Catalog Handbook of Fine Chemicals, 1996–97.*
Lucia Helena B. Baptistella, et al., "1,8–Diazabicyclo[5.4.0] Undec–7–Ene As A Mild Deprotective Agent for Acetyl Groups", Synthesis, No. 6, pp. 436–438, 1989. XP–002152124.

* cited by examiner

Primary Examiner—Alan L. Rotman
Assistant Examiner—Hector M Reyes
(74) Attorney, Agent, or Firm—Oblon, Spivak, McClelland, Maier & Neustadt, P.C.

(57) ABSTRACT

Isobornyl (meth)acrylate is synthesized by a two-stage one-pot process, wherein isobornyl acetate is converted to isoborneol followed by transesterification with (meth) acrylic acid methyl ester, without isolation of the intermediates or purification of the product.

21 Claims, No Drawings

US 6,479,696 B1

METHOD FOR SYNTHESIS AND PROCESS INHIBITION OF ISOBORNYL (METH) ACRYLATE

BACKGROUND OF THE INVENTION

1. Field of the Invention

The invention relates to a method for synthesis and process inhibition of isobornyl (meth)acrylate, which is widely used as a monomer for manufacture of, for example, varnish binding agents.

2. Discussion of the Background

Conventionally, camphene is reacted with methacrylic acid in the presence of an acid catalyst to yield isobornyl (meth)acrylate. For example, German Patent DE 44 19 686 (Hoechst AG) describes a process for the synthesis of terpene esters by reacting camphene and a low molecular weight carboxylic acid using an acid ion exchanger as a catalyst. The reagents are passed in ascending flow through a column-type reactor containing a bed of acid ion exchanger. However, a disadvantage in this process is the loss of activity of the catalyst after several reaction cycles. Attempts to compensate for this loss by raising the temperature have the disadvantage of increasing the polymerization of the unsaturated carboxylic acids on the catalyst, leading in time to irreversible deactivation of the catalyst. The process is therefore not suitable for large-scale industrial applications, which require long catalyst lives.

European Patent EP 718 271 (Elf Atochem) also describes the synthesis of isobornyl methacrylate or acrylate by reacting camphene with acrylic acid or (meth)acrylic acid in the presence of an acid ion exchange catalyst. Although ion exchange catalysis seems elegant at first sight, in industrial practice it has the disadvantage that the ion exchanger loses activity after repeated use, since it becomes coated with polymer despite good process stabilization. Regenerative cleaning and activation, for example by washing with acid or a suitable solvent for drying such as acetone, does not restore the original activity level. Accordingly, the catalyst must be replaced after a few cycles of use, unless poorer conversion is acceptable.

According to the method of Japanese Laid-Open Application JP-0S 54-126293, only 10% conversion is achieved. In view of the relatively expensive starting materials, such low conversion during the reaction is economically impractical. Satisfactory conversions can be achieved with 75% sulfuric acid when the reaction mixture is very strongly inhibited. The benefit of inhibition of the reaction mixture is offset by disadvantages in regard to the product, which becomes correspondingly difficult to polymerize.

A further alternative to the synthesis of isobornyl (meth) acrylate is transesterification of methyl methacrylate starting from isoborneol. The process of transesterification of methyl methacrylate to obtain esters of (meth)acrylic acid is known.

German Patent DE 196 02 035 (Rohm GmbH) describes the transesterification of (meth)acrylic acid esters of short-chain alcohols with long-chain alcohols ($C_1$ to $C_{28}$) to obtain (meth)acrylic acid esters of long-chain alcohols in the presence of a transesterification catalyst comprising $Ca(OH)_2$ or a mixture of $Ca(OH)_2$ and LiCl.

Furthermore, German Patent DE 19 54 709, Röhm GmbH describes a catalytic process for transesterification of (meth) acrylic acid esters using at most 250 ppm of $Ca(OH)_2$ as a catalyst.

German Patent DE 195 45 870 (Röhm GmbH) discloses a transesterification of lower (meth)acrylic acid esters to (meth)acrylic acid esters of carbohydrates having at least one free hydroxyl group. A mixture of alkali metal carbonate and a quaternary ammonium salt is used as the transesterification catalyst.

German Patent DE 44 011 32 (Röhm GmbH) describes the transesterification of (meth)acrylic acid esters with alcohols which contain one or more esterifiable hydroxyl groups in the presence of a mixed catalyst comprising 5 to 95 mol % of diorganyltin oxide and 95 to 5 mol % of diorganyltin dihalides. The mixed catalyst is used in proportions of between 0.01 and 10 wt % based on the weight of the reaction mixture.

German Patent DE 43 01 673 (Röhm GmbH) describes the use of a lead compound as the transesterification catalyst. Dialkyltin oxide alone as the transesterification catalyst has also already been described (German Patent DE 4010532, Röhm GmbH).

The esterification of an aqueous (meth)acrylic acid (water content: 5 to 60 wt %) with an alkanol to obtain the corresponding (meth)acrylic acid esters is disclosed in German Patent DE 31 46 191 (Röhm GmbH). In this process the aqueous (meth)acrylic acid is passed into a boiling esterification mixture containing $H_2SO_4$ or an organic sulfonic acid and the resulting ester is distilled off.

U.S. Pat. No. 3,087,962 (Rohm & Haas) describes the synthesis of esters of acrylic acid or of methacrylic acid by esterification of acrylic acid or methacrylic acid under catalysis by $H_2SO_4$ and $BF_3$.

According to the known transesterification procedures, isobornyl methacrylate is obtained in high purity and good yield from isoborneol and (meth)acrylic acid methyl ester in a smooth reaction. Isoborneol is not commercially available. However, isobornyl acetate, which is also used as a scent, can be obtained inexpensively in the market. Tests have shown that isobornyl acetate cannot be reacted with either methyl (meth)acrylate or (meth)acrylic acid to obtain isobornyl (meth)acrylate by means of the standard procedure of adding a known transesterification catalyst.

SUMMARY OF THE INVENTION

It is an objective of the present invention to find, preferably starting from inexpensive raw materials, an industrially feasible synthesis of isobornyl (meth)acrylate which can be performed without the use of complex mixed catalysts and which does not require excessive stabilization of the reaction mixture.

These and other objects are achieved according to the invention, the first embodiment of which includes a process for the synthesis of isobornyl (meth)acrylate, comprising:

reacting isobornyl acetate with a compound having a hydroxyl group in a reaction mixture to obtain isoborneol;

reacting said isoborneol with a (meth)acrylic acid ester thereby obtaining isobornyl (meth)acrylate.

DETAILED DESCRIPTION OF THE INVENTION

It has now been found that isobornyl acetate, which is used as a scent and which is commercially available, can be converted to isobornyl methacrylate. However, isobornyl acetate cannot be reacted with either methyl (meth)acrylate or (meth)acrylic acid to obtain isobornyl (meth)acrylate by means of the known procedures of adding a transesterification catalyst.

A simple isobornyl (meth)acrylate synthesis is successful if isobornyl acetate 1 is reacted in a first stage with methanol 2 and a transesterification catalyst in a one-pot process to obtain isoborneol 3 and methyl acetate 4. This reaction step is followed by addition of methyl (meth)acrylate 5 in the presence of the same catalyst as in stage 1, whereby isobornyl (meth)acrylate 6 is produced. The intermediate products are not isolated. The raw ester is already formed in very pure condition. Purification by distillation is not necessary. However, the reaction can be followed by an additional purification step.

Lead compounds, zinc compounds, alkaline earth metal oxides or alkaline earth metal hydroxides, such as CaO, $Ca(OH)_2$, MgO, $Mg(OH)_2$ or mixtures of the aforesaid compounds, as well as alkali metal hydroxides, alkoxides and LiCl can be used as transesterification catalysts. Mixtures of the aforesaid alkaline earth metal compounds and the Li salts can be used as transesterification catalysts. A mixture of 75% by weight of calcium oxide and 25% by weight of lithium hydroxide per 100% by weight of the catalyst mixture is preferred. The catalyst mixture can include 50, 55, 60, 65, 70, 75, 80, 85, 90 and 95% by weight of calcium oxide including all values therebetween based on the weight of the catalyst mixture. Furthermore, the catalyst mixture can include 5, 10, 15, 20, 25, 30, 35, 40, 45 and 50% by weight of lithium hydroxide including all values and subvalues therebetween based on the total weight of the catalyst mixture.

The proportion of catalyst or mixture of catalysts ranges between 0.01% by weight and 10% by weight based on the weight of the reaction mixture at the beginning of the reaction. A proportion of 0.5% by weight to 5% by weight is preferred, and a proportion of 1% by weight to 3% by weight is especially preferred. The proportion of catalyst or catalyst mixture can include all values and subvalues therebetween especially including 0.02, 0.05, 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0 and 9.5% by weight based on the weight of the reaction mixture at the beginning of the reaction.

Isobornyl (meth)acrylate can be obtained with a purity of at least 85%, preferably at least 90%, more preferably at least 95% and most preferably at least 99%. The purity includes all values and subvalues therebetween, especially including 86, 88, 90, 92, 94, 96 and 98%.

Preferred hydroxyl compounds are monohydric alcohols, dihydric alcohols and polyfunctional alcohols. Preferably, ethanol or propanol are used as hydroxyl compounds. Most preferably, methanol is used as a compound having a hydroxyl group.

Hydroquinone monomethyl ether, octadecyl-3-(3,5-di-tert-butyl-4-hydroxyphenyl) propionate and 4-hydroxy-2,2,6,6-tetramethylpiperidyl-N-oxyl are preferably used as stabilizers.

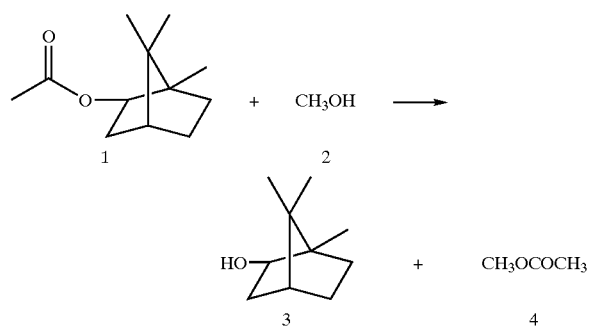

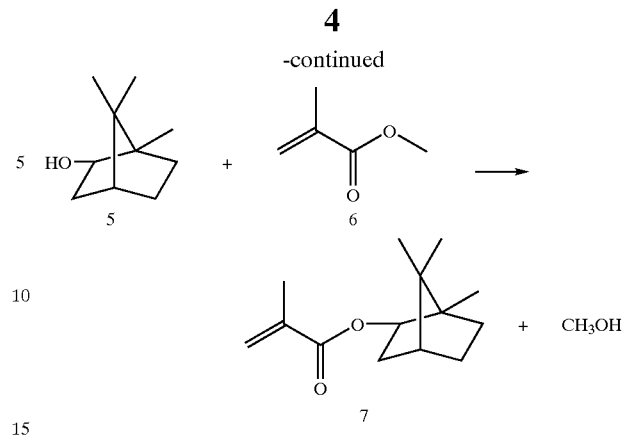

Having generally described this invention, a further understanding can be obtained by reference to certain specific examples which are provided herein for purposes of illustration only, and are not intended to be limiting unless otherwise specified.

EXAMPLE

Example 1

In a 500 ml four-necked flask with mechanical stirrer, internal thermometer, 30 cm packed column (containing Raschig rings) with automatic column head and gas inlet tube as well as oil-bath heater there was placed 196 g (1 mol) of isobornyl acetate. Then 480 g (15 mol) of methanol and, as catalysts, 4.7 g of calcium oxide and 2 g of lithium hydroxide (totaling 1% relative to the total initial weight) were added. The mixture was heated to boiling under an inflow of nitrogen, and a mixture of methyl acetate and methanol was drawn off over the column head in a head temperature range of 57 to 65° C. (duration 7 hours). Thereafter the residual methanol was distilled off and then 500 g (5 mol) of methyl (meth)acrylate (MMA), 0.033 g of hydroquinone monomethyl ether and 0.002 g of 4-hydroxy-2,2,6,6-tetramethylpiperidyl-N-oxyl were added. Air was now passed in instead of nitrogen, and the mixture was heated to boiling once again. The resulting methanol-MMA azeotrope was drawn off from 64 to 100° C. (head temperature) in 6 hours. The contents were then allowed to cool, the residual MMA was removed in the rotary evaporator, and the catalyst was separated by pressure filtration. There was obtained 179 g (81% of theory), of isobornyl (meth)acrylate with a purity of 94.7 vol % as determined by gas chromatography.

Example 2

The procedure was the same as in Example 1, but without $N_2$ inflow. Using a 2-liter reaction vessel, 521 g (2.5 mol) of isobornyl acetate, 600 g (18 mol) of methanol, 3.36 g of LiOH, 7.85 g of CaO, 1.25 kg (12.5 mol) of MMA, 0.083 g of hydroquinone monomethyl ether and 0.006 g of 4-hydroxy-2,2,6,6-tetramethylpiperidyl-N-oxyl were reacted. There was obtained 443 g (80% of theory) of isobornyl (meth)acrylate with a purity of 96.7% as determined by gas chromatography. The product was then fractionated under addition of 20 ppm 4-hydroxy-2,2,6,6-tetramethylpiperidyl-N-oxyl and 500 ppm octadecyl-3-(3,5-di-tert-butyl-4-hydroxyphenyl) propionate at 10 mbar pressure over a 20 cm Vigreux column. There was obtained 390 g of isobornyl (meth)acrylate, with a purity of 98%.

Comparison Example 3

Conventional transesterification from isobornyl acetate, which does not lead to the (meth)acrylate.

In the apparatus described in Example 1 (1-liter reaction vessel, reflux condenser instead of column) there were placed 196 g (1 mol) of isobornyl acetate and 344 g (4 mol) of (meth)acrylic acid. As inhibitors there were added 0.044 g of hydroquinone monomethyl ether, 0.222 g of octadecyl-3-(3,5-di-tert-butyl-4-hydroxyphenyl) propionate and 0.004 g of 4-hydroxy-2,2,6,6-tetramethylpiperidyl-N-oxyl. As catalysts there were added 2.5 g of dioctyltin oxide and 2.9 g of dioctyltin dichloride. The contents were heated to 140° C. for 6 hours under air inflow. Thereafter a gas chromatogram of the flask contents was run. Isobornyl (meth)acrylate was not detectable.

Comparison Example 4

Conventional transesterification from isobornyl acetate, which does not lead to the (meth)acrylate.

The above comparison example was performed with 400 g of methyl (meth)acrylate instead of (meth)acrylic acid (catalysts: 2.8 g of dioctyltin and 3.2 of dioctyltin dichloride). The mixture was stirred under air inflow for 6 hours at 90° C. No methyl acetate was formed, and therefore no transesterification occurred.

Comparison Example 5

Conventional transesterification from isobornyl acetate, which does not lead to the (meth)acrylate.

Example 4 was repeated, but the column from Example 1 was used instead of the reflex condenser and 6 g of sodium methanolate was used as the catalyst. The mixture was heated to boiling, and MMA was distilled off over the column head then tested for methyl acetate by GC. Despite further addition of 50 g of methanol (after a reaction time of 5 hours) and 3 g of sodium methanolate (after 8 hours), no methyl acetate was detected within a reaction time of 14 hours.

The priority document of the present application, German patent application, DE 199 30 721.0 filed Jul. 5, 1999, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A process for the synthesis of isobornyl (meth)acrylate, comprising
   (a) reacting in a container isobornyl acetate with a compound having a hydroxyl group in a reaction mixture in the presence of a transesterification catalyst to obtain isoborneol;
   (b) reacting said isoborneol remaining in said container with a (meth)acrylic acid ester added into said container in the presence of said transesterification catalyst remaining in said container to obtain isobornyl (meth)acrylate.

2. The process according to claim 1, wherein said isobornyl (meth)acrylate is obtained without further purification.

3. The process according to claim 1, wherein said isobornyl (meth)acrylate has a purity of at least 90%.

4. The process according to claim 1, wherein said isobornyl (meth)acrylate has a purity of at least 95%.

5. The process according to claim 1, wherein said isobornyl (meth)acrylate has a purity of at least 99%.

6. The process according to claim 1, wherein said transesterification catalyst is selected from the group consisting of a lead compound, a zinc compound, an alkaline earth metal oxide, an alkaline earth metal hydroxide, an alkaline metal hydroxide, an alkoxide, an alkali metal halide and mixtures thereof.

7. The process according to claim 6, wherein said alkaline earth metal oxide is CaO or MgO.

8. The process according to claim 6, wherein said alkaline metal hydroxide is $Ca(OH)_2$ or $Mg(OH)_2$.

9. The process according to claim 6, wherein said alkaline metal halide is lithium chloride.

10. The process according to claim 6, wherein said alkaline metal hydroxide is lithium hydroxide.

11. The process according to claim 1, wherein said transesterification catalyst is a mixture of 75% by weight of calcium oxide and 25% by weight of lithium hydroxide per 100% by weight of said transesterification catalyst.

12. The process according to claim 1, wherein an amount of said transesterification catalyst is 0.01–10% by weight per 100% by weight of said reaction mixture.

13. The process according to claim 1, wherein an amount of said transesterification catalyst is 0.5–5% by weight per 100% by weight of said reaction mixture.

14. The process according to claim 1, wherein an amount of said transesterification catalyst is 1–3% by weight per 100% by weight of said reaction mixture.

15. The process according to claim 1, wherein said compound having a hydroxyl group is selected from the group consisting of a monohydric alcohol, a dihydric alcohol, a polyfunctional alcohol and mixtures thereof.

16. The process according to claim 15, wherein said monohydric alcohol is ethanol, propanol or a mixture thereof.

17. The process according to claim 15, wherein said monohydric alcohol is methanol.

18. The process according to claim 1, wherein said (meth)acrylic acid ester is methyl (meth)acrylate.

19. A process for the synthesis of isobornyl (meth)acrylate, comprising
   (a) reacting in a container isobornyl acetate with a compound having a hydroxyl group in a reaction mixture in the presence of a transesterification catalyst to obtain isoborneol;
   (b) removing by-products of the reaction in step (a) to obtain said isoborneol in said transesterification catalyst in said container;
   (c) reacting said isoborneol remaining in said container with a (meth)acrylic acid ester added into said container in the presence of said transesterification catalyst remaining in said container to obtain isobornyl (meth)acrylate.

20. A process for the synthesis of isobornyl (meth)acrylate, comprising
   (a) reacting in a container isobornyl acetate with methanol in a reaction mixture in the presence of a transesterification catalyst to obtain isoborneol and methyl acetate;
   (b) reacting said isoborneol remaining in said container with a (meth)acrylic acid ester added into said container in the presence of said transesterification catalyst remaining in said container to obtain isobornyl (meth)acrylate.

21. A process for the synthesis of isobornyl (meth)acrylate, comprising
   (a) reacting in a container isobornyl acetate with methanol in a reaction mixture in the presence of a transesterification catalyst to obtain isoborneol and methyl acetate;

(b) removing by-product methyl acetate of the reaction in step (a) to obtain said isoborneol in said transesterification catalyst in said container;

(c) reacting said isoborneol remaining in said container with a (meth)acrylic acid ester added into said container in the presence of said transesterification catalyst remaining in said container to obtain isobornyl (meth)acrylate.

* * * * *